(12) United States Patent
Roxendal et al.

(10) Patent No.: US 6,417,427 B1
(45) Date of Patent: *Jul. 9, 2002

(54) ABSORBENT ARTICLE HAVING LAYER OF CONTINUOUS FIBERS BONDED IN A PATTERN

(75) Inventors: Sofia Roxendal, Pixbo; Peter Rönnberg, Molndal; Roy Hansson, Mölndal, all of (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/328,455

(22) Filed: Jun. 9, 1999

(30) Foreign Application Priority Data

Dec. 3, 1997 (SE) ................................ 9704484

(51) Int. Cl.[7] ................................. A61F 13/15
(52) U.S. Cl. .................... 604/378; 604/379; 604/380
(58) Field of Search ................. 604/382, 378, 604/365, 374, 366, 383, 384, 385.23; 428/170, 171, 122, 167

(56) References Cited

U.S. PATENT DOCUMENTS

| 4,676,786 A | * | 6/1987 | Nishino ...................... 604/378 |
| 5,662,633 A | * | 9/1997 | Doak et al. ................. 604/378 |
| 5,669,895 A | * | 9/1997 | Murakami et al. .......... 604/380 |
| 5,972,505 A | * | 10/1999 | Phillips et al. ............. 428/397 |

* cited by examiner

Primary Examiner—John G. Weiss
Assistant Examiner—Jacqueline F Stephens
(74) Attorney, Agent, or Firm—Burns, Doane, Swecker & Mathis, L.L.P.

(57) ABSTRACT

Absorbent article, such as a diaper, pant diaper, incontinence guard, sanitary napkin, wound dressing and the like, comprising a layer of continuous fibres, so-called tow, which have been bonded together in points, lines or spots in a bonding pattern (10), but otherwise are substantially unbonded to each other, wherein the bonding pattern (10) is different in different portions of said layer (5). The layer can either be utilized as a liquid acquisition layer (5) in the article underneath a topsheet (2), as a topsheet (12), or as a combined topsheet and liquid acquisition layer (22).

29 Claims, 7 Drawing Sheets

ABSORBENT ARTICLE HAVING LAYER OF CONTINUOUS FIBERS BONDED IN A PATTERN

TECHNICAL FIELD

The present invention relates to an absorbent article, such as a diaper, pant diaper, incontinence guard, sanitary napkin, wound dressing and the like, of the kind comprising a liquid pervious top layer, a liquid impervious back layer and an absorbent body arranged therebetween.

BACKGROUND OF THE INVENTION

Absorbent articles of the above-mentioned kind are intended for absorption of body fluids, such as urine and blood. As a liquid pervious topsheet, facing the wearer during use, they usually exhibit a nonwoven material, for example of spunbond-type. It is also previously known to arrange a liquid acquisition layer between the top layer and the absorbent body, said liquid acquisition layer having the ability to quickly receive large quantities of liquid, and to distribute the liquid and temporarily store it before it is absorbed by the underlying absorbent body. This is of great importance, especially in the thin compressed absorbent bodies of today, often comprising a high content of so called superabsorbents, which certainly have a high absorption capacity but in many cases a too low absorption rate in order to momentously be able to absorb the large quantity of liquid which can be discharged within a few seconds during urination. A porous, relatively thick acquisition layer, for example in the form of a fibrous wadding, a carded fibrous web, or another type of fibrous material, has a high instantaneous liquid-receiving capacity and is able to store the liquid temporarily until it has been absorbed by the absorbent body. The same applies for porous foam materials. The liquid is thereafter drained successively into the adjacent absorbent body, after which the acquisition layer once again has the capacity to receive liquid from a repeated wetting.

Examples of absorbent articles comprising such porous acquisition layers are, for example, disclosed in U.S. Pat. No. 3,371,667, EP-A-0,312,118 and EP-A-0,474,777.

The materials used today as acquisition layers in absorbent articles are mostly functioning well, but are relatively expensive and can sometimes exhibit an insufficient acquisition rate, especially in the second and third wettings, if large quantities of liquid are involved. Furthermore, they are difficult to process and store due to their bulkiness.

It is previously known through EP-A-0,391,814 and GB-B-2,209,672 to use continuous, unbonded synthetic fibres, so-called tow, in absorbent articles for distributing liquid in the longitudinal direction of the article.

Another problem is that conventional liquid pervious topsheet materials used for absorbent articles of this kind, normally a nonwoven material of synthetic fibres, e.g. a spunbond material, often exhibit a lower acquisition rate for liquid than the acquisition layer, wherein liquid can leak out from the article before it reaches the acquisition layer. Furthermore, the liquid is retained in capillaries in a dense topsheet of nonwoven and a more porous acquisition layer, e.g. wadding, cannot drain liquid from the topsheet. This problem can of course be solved by means of using a topsheet material which is very open and therefore has a high liquid permeability. Such an open topsheet material can, however, cause problems with too low strength and sharp fibre ends from the acquisition layer which may penetrate the open topsheet material and irritate the user.

OBJECT AND MOST IMPORTANT FEATURES OF THE INVENTION

The object of the present invention is to provide a material which exhibits a high acquisition rate for liquid also when repeatedly wetted, exhibits a high strength and wear resistance, high comfort, high processability and has a relatively low price. Furthermore, it should be possible to combine different wishes, concerning the liquid acquiring and liquid distributing properties, in the same material. According to the invention, this has been achieved by means of a layer of continuous fibres, so-called tow, which have been bonded together in points, lines or spots in a bonding pattern, but otherwise are substantially unbonded to each other, wherein the bonding pattern is different in different portions of said layer.

According to a preferred embodiment, the bonding pattern is more sparse in the central portion of the layer, intended to constitute the liquid acquisition area of the article, and denser in one or several of the edge portions of the layer. Thereby, a rapid liquid acquisition can be obtained in the central portions of the layer, while liquid leakage from the edge portions of the layer is rendered more difficult.

Furthermore, since the liquid distributing ability of the material in the longitudinal direction of the fibres is very high, it is advantageous if the bonding pattern, along the transversely to the longitudinal direction of the continuous fibres extending edge portions of the article, exhibits a high density which essentially prevents liquid from spreading, whereby edge leakage can be prevented.

Preferably, the bonding pattern in said transversely extending edge portion comprises at least one continuous barrier line which prevents liquid from spreading.

According to a preferred embodiment, the bonding pattern along the encompassing edge portions of the layer exhibit a high density, which essentially prevents liquid from spreading, and according to still another embodiment, the bonding pattern exhibits at least one continuous barrier line in said encompassing edge portion which prevents liquid from spreading.

Furthermore, the layer can exhibit one or several continuous directing lines intended to achieve a controlled liquid distribution in the layer.

The bonding pattern may further be designed so that the layer obtains a three-dimensional shape, for example a bowl-shape or a raised central portion.

The bonding pattern is preferably non-random.

The layer can be used as a liquid acquisition layer underneath a topsheet, as a topsheet, or as an integrated topsheet/liquid acquisition layer.

Further features of the invention are evident from the following description and the claims.

DESCRIPTION OF THE DRAWINGS

In the following, the invention will be described in greater detail, with reference to embodiments shown in the accompanying drawings.

DESCRIPTION OF EMBODIMENTS

Figure 1:
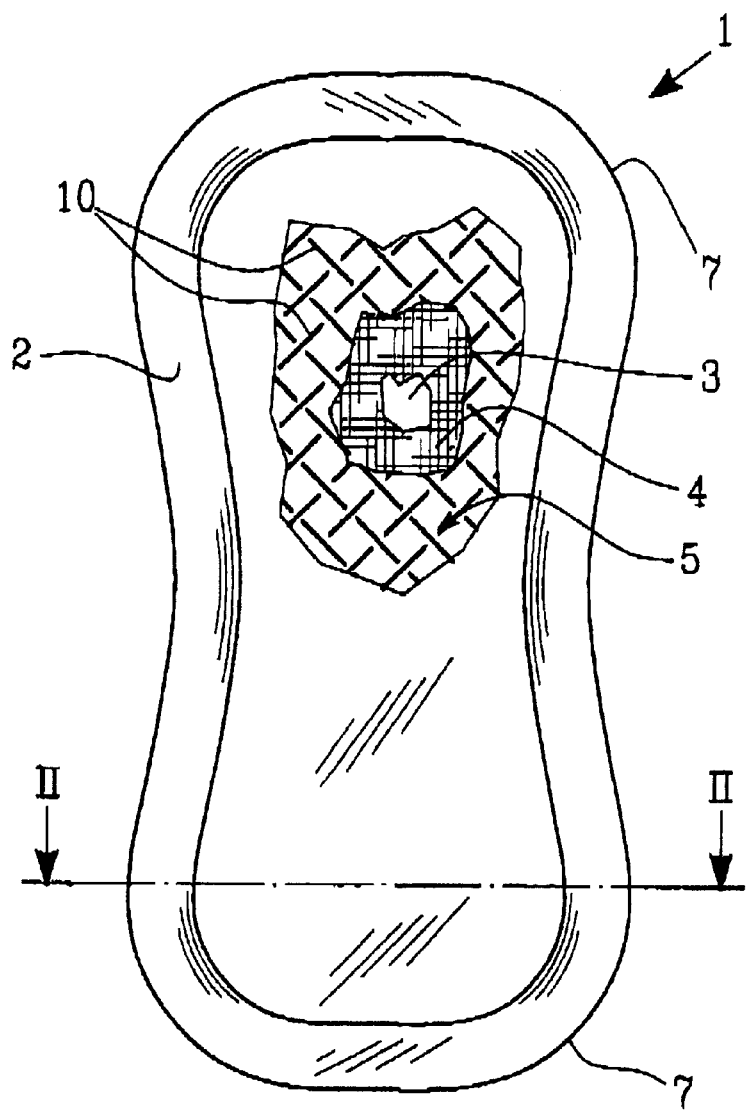
FIG. 1 is a plan view of an embodiment of an absorbent article according to the invention in the form of an incontinence guard.
Figure 2:
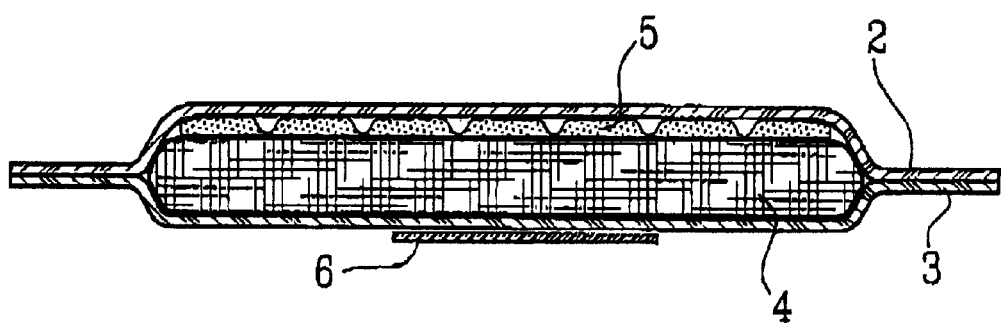
FIG. 2 is a section along the line II—II in FIG. 1.

In FIGS. 1 and 2, an embodiment of an incontinence guard 1 is shown, which comprises a liquid pervious top layer 2, a liquid impervious back layer 3 and an absorbent body 4 enclosed therebetween. Furthermore, a porous and resilient liquid acquisition layer 5 is arranged between the liquid pervious top layer 2 and the absorbent body 4.

The liquid pervious top layer 2 can consist of a perforated plastic film or a nonwoven material, for example a spunbond material of synthetic filaments, a melt-blown material, a thermally bonded material or a bonded carded fibrous material. The liquid impervious back layer 3 can consist of a plastic film, a nonwoven material coated with a liquid impervious material, or a hydrophobic nonwoven material which resists liquid penetration.

The top layer 2 and the back layer 3 have a slightly larger extension in the plane than the absorbent body 4 and the liquid acquisition layer 3, and extend outside the edges of these. The layers 2 and 3 are interconnected within the projecting portions, for example by means of gluing or welding with heat or ultrasonic.

The absorbent body 4 can be of any conventional type. Examples of commonly occurring absorption materials are cellulosic fluff pulp, tissue layers, highly absorbent polymers (so-called superabsorbents), absorbent foam materials, absorbent nonwoven materials, and the like. It is common to combine cellulosic fluff pulp with superabsorbents in an absorbent body. It is also common with absorbent bodies comprising layers of different materials with different properties, when liquid acquisition ability, liquid distributing ability and liquid storage capacity are concerned. This is well-known to the person skilled in the art and therefore need not be described in detail. The thin absorbent bodies, which are common in for example baby diapers and incontinence guards, often consist of a compressed, mixed or layered, structure of cellulosic fluff pulp and superabsorbent.

On the outside of the liquid impervious back layer 3, fastening means in the form of longitudinal strings 6 of a self-adhesive glue are arranged. Before use, the adhesive regions 6 are suitably protected by a removable protective strip, not shown in the drawings, of paper or plastic film treated with a release agent. In the shown embodiment, the fastening means consist of longitudinal adhesive regions. A number of other adhesive patterns, e.g. transverse patterns, are of course conceivable, as well as other types of fastening means, such as hook and loop surfaces, snap fasteners, frictional fixation, girdles, special underpants, or the like.

An incontinence guard of the type shown in FIG. 1 primarily is intended to be used by persons suffering from relatively light incontinence troubles, and is easily accommodated inside a pair of ordinary underpants. Thereby, the fastening means 6 serve to keep the incontinence guard in its place inside the underpants during use.

The incontinence guard 1 is hourglass-shaped with wider end portions 7 and a narrower crotch portion 8, located between the end portions. The crotch portion 8 is the portion of the incontinence guard which during use is intended to be applied in the crotch region of the user and serve as a receiving area for the excreted body fluid.

Figure 3:
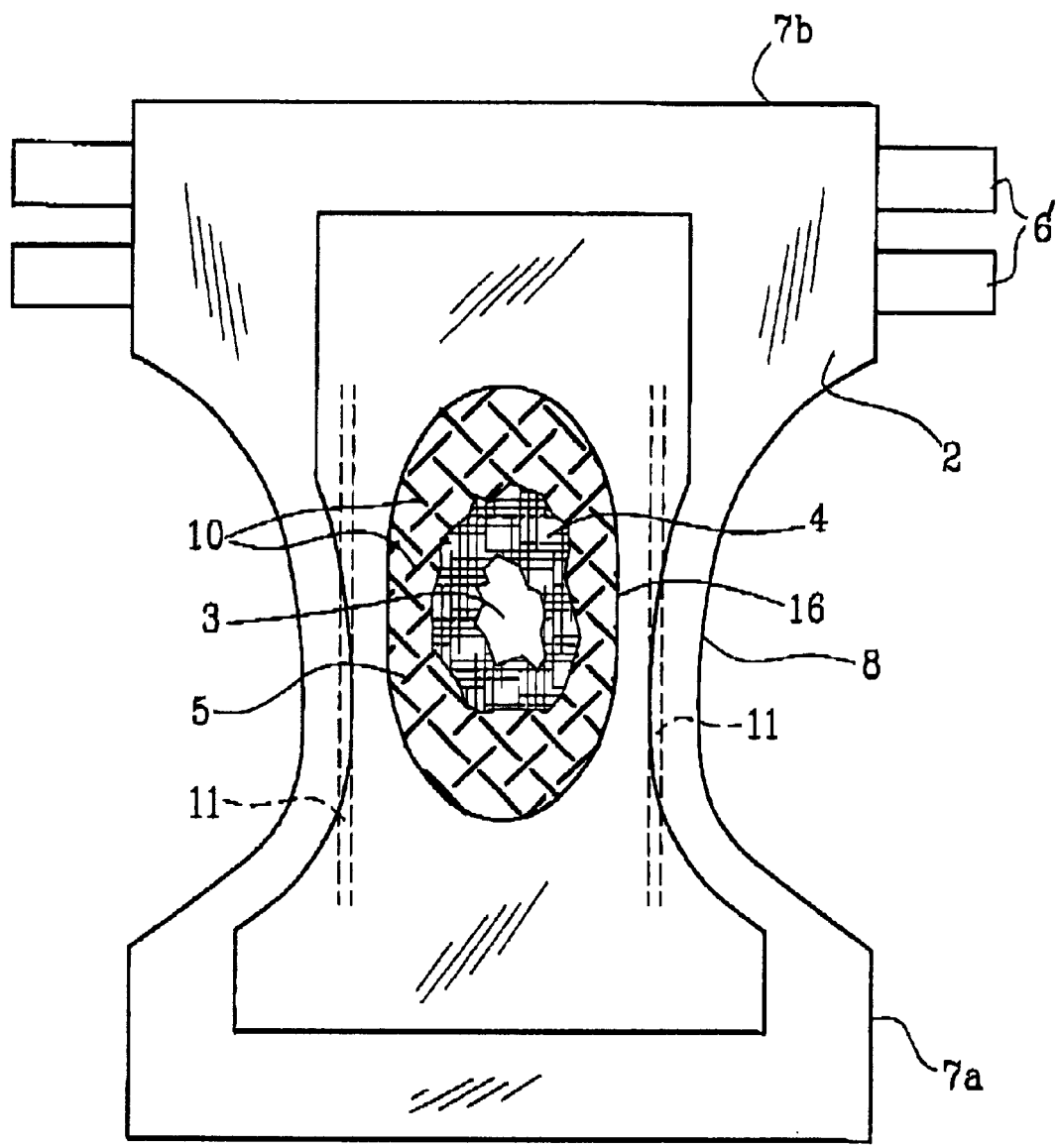
FIG. 3 shows, in plan view, an absorbent article in the form of a diaper.

In FIG. 3, an absorbent article in the form of a diaper is shown which, like the above-described incontinence guard, comprises a liquid pervious top layer 2, a liquid impervious back layer 3 and an absorbent body 4 enclosed therebetween, and further comprises an acquisition layer 5 applied between the top layer 2 and the absorbent body 4. In the shown example, the top layer is provided with a hole 16, positioned in the intended wetting area, whereby the acquisition layer 5 is exposed directly towards the user in this area. Instead of one hole 16, several smaller holes can be provided.

The diaper is intended to enclose the lower part of the trunk of the user as a pair of absorbent pants. It exhibits a front portion 7a intended to be facing forward on the user during use, a back portion 7b intended to be facing backwards on the user during use, and a narrower crotch portion 8, located between the front and the back portions, which is intended to be applied in the crotch region of the user, between his/her legs. In order to enable the diaper to be brought into and fixed in the desired pant shape, tape tabs 6' are arranged close to the rearwardly waist edge of the diaper, whereby the diaper is kept together around the waist of the user. Other fastening means, such as hook and loop means, hooks, etc., are of course conceivable.

It should be noted that the incontinence guard and the diaper, shown in the drawings and described above, only are two non-limiting examples of an absorbent article. Accordingly, the shape of the article, as well as its design otherwise, can be varied. The absorbent article can also be constituted of a pant diaper, a sanitary napkin, a wound dressing, or the like. The absorbent article can either be of disposable or reusable type. For products of the reusable type, however, other materials than the above-described are relevant as a liquid pervious top layer and as an absorbent body, respectively.

A porous and resilient acquisition layer 5, having the ability to rapidly receive large quantities of liquid and to distribute the liquid and store it temporarily before it is absorbed by the underlying absorbent body 4, is arranged between the liquid pervious top layer 2 and the absorbent body 4. This ability should essentially be maintained also after wetting of the material. The acquisition layer 5 can cover either the entire absorbent body 4, extend outside it, or cover only the central portions of the absorbent body.

According to the invention, the acquisition layer is constituted of a layer 5 of continuous fibres 9, so-called tow, which have been bonded together in points, lines or spots in a bonding pattern 10, but otherwise are substantially unbonded to each other. In the embodiment shown in FIG. 1, the bonding pattern 10 is constituted of a line pattern with short lines arranged in a zigzag configuration. The bonding pattern is achieved by means of, for example, ultrasonic welding or other thermal bonding. Examples of other suitable thermal bonding methods are pattern calendering, laser bonding etc. A prerequisite for this is that at least part of the fibres in the tow are thermoplastic. Examples of thermoplastic fibres are polyolefines, polyamides, polyester and the like. Also so-called bi-component fibres can be included. As an alternative to thermal bonding, bonding can be achieved by means of a binding agent, using so-called print-bonding or dot-bonding, or mechanically by means of so-called entanglement, using needling or water jets. The choice of bonding type is primarily decided by the type of fibres which are used in the tow.

The design of the bonding pattern 10 can of course vary within wide limits. The pattern may be in the form of points, spots or preferably lines. The lines may be straight, as well as curved, and the length can vary, from a few millimetres to the lines extending transversely or diagonally across the entire article. Preferably, the lines extend transversely or obliquely across the longitudinal direction of the fibres 9, so that a plurality of fibres are bonded to each other by each bonding line. It is also an advantage if different bonding lines overlap each other, as seen in the cross-direction of the fibres, so that a main part of the fibres are bonded at least along a part of their length.

According to the invention, the bonding pattern is different in different portions of the layer 5. Accordingly, the bonding pattern may for example be more sparse in the wetting area and more dense outside of this. It is also possible to design the bonding pattern in such a way that the layer 5 obtains different height (thickness) in different portions of the article, for example lower in the central portions and higher in the surrounding edge portions in order to create a bowl-shape which provides a liquid receiving volume or, alternatively, so that the layer obtains a raised central portion which creates a closer body contact and by means of this a decreased risk of leakage. This will be described in greater detail below with reference to FIGS. 10–13.

Fibre tow is supplied in bags, or in the form of bales or rolls of continuous fibres, which either are straight, crimped or curled. Crimped or curled fibres are preferred in this case, since they result in a very open and lofty structure. The bales or the like are opened in special converting devices, wherein the fibres are separated from each other, stretched and distributed into an essentially uniformly thick layer. The layer 5 is bonded in the desired bonding pattern, as described above, and is cut into suitable lengths. Alternatively, the bonding can take place after the cutting. Tow is a relatively cheap delivery form for fibres, in comparison with nonwoven, waddings, or the like, which normally are used as acquisition materials.

Figure 4:
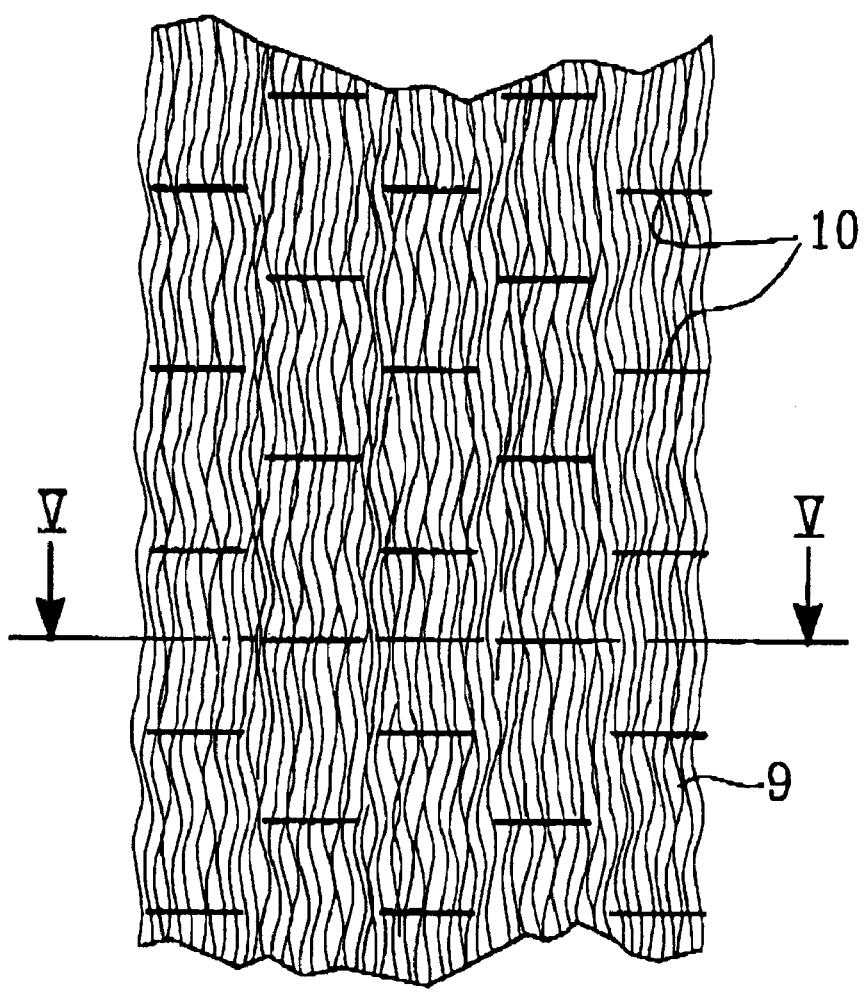
FIG. 4 schematically shows a portion of a fibrous layer according to the invention.
Figure 5:
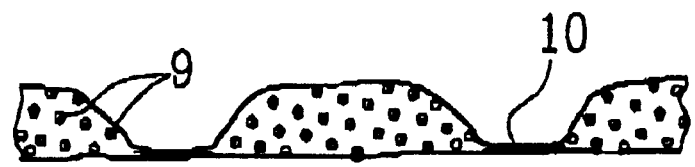
FIG. 5 shows, in magnification, a schematic section along the line IV—IV in FIG. 3.

In FIGS. 4 and 5, a portion of a layer 5 of fibre tow is shown, which has been bonded in a simple bonding pattern 10 with transverse, short lines. The fibres 9 are unbonded to each other except at the bonding sites.

The fibres in the tow can be of any suitable material, such as polyethylene, polypropylene, polyamide, polyester, polyvinyl acetate, cellulose acetate, regenerated cellulosic fibres such as viscose and rayon, or of bi-component type, with a shell of a polymer having a lower melting point and a core of a polymer having a higher melting point. Fibres which exhibit a high resiliency, for example polyester, co-polyester and polypropylene, are particularly preferred.

The fibre thickness can vary, but is suitably within the interval 0.5 to 50 dtex, preferably 1.5 to 25, and most preferably 2 to 15 dtex, if the material is to be used as an acquisition material. The open, lofty structure in combination with the relatively coarse fibre dimension provides a very rapid liquid acquisition. In addition, the material is strong due to the longitudinal continuous fibres, which provide strength in the longitudinal direction, and the bonding pattern, which provides strength in the transverse direction.

Figure 6:
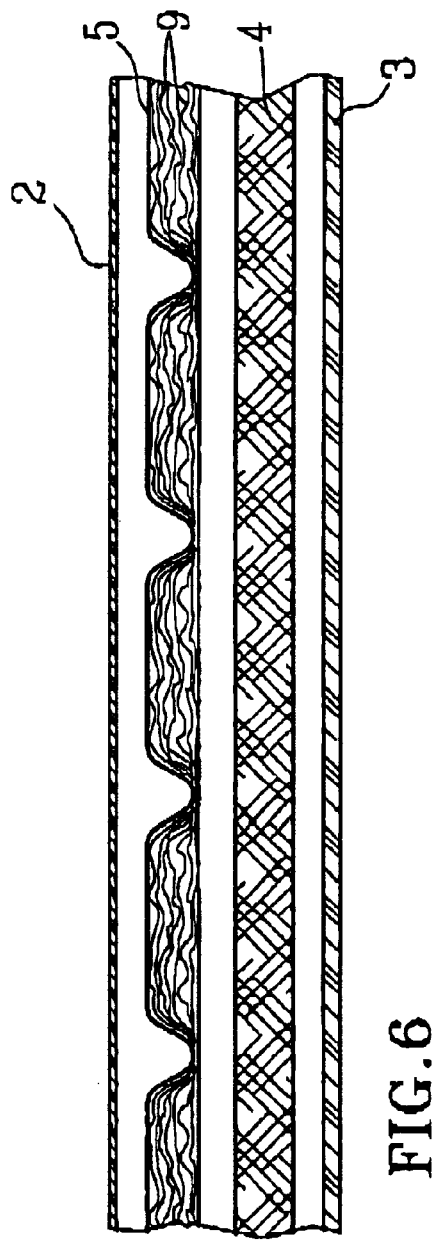
FIGS. 6–9 are schematic, exploded cross-sectional views in the longitudinal direction of four different embodiments of the article according to the invention.

In the above disclosed example, the material layer 5 has been used as an acquisition layer 5 underneath a liquid pervious top layer 2. This is also shown in FIG. 6. In this case, the basis weight of the bonded fibre-tow should be at least 10 g/m$^2$, preferably be within the interval 10–1000 g/m$^2$, more preferably 30–700, and most preferably 30–350 g/m$^2$. The top layer 2 can be of any optional type, but preferably exhibits a relatively open structure which permits a rapid liquid acquisition. The top layer 2 can be bonded to the acquisition layer 5 in the bonding points 10.

Figure 7:
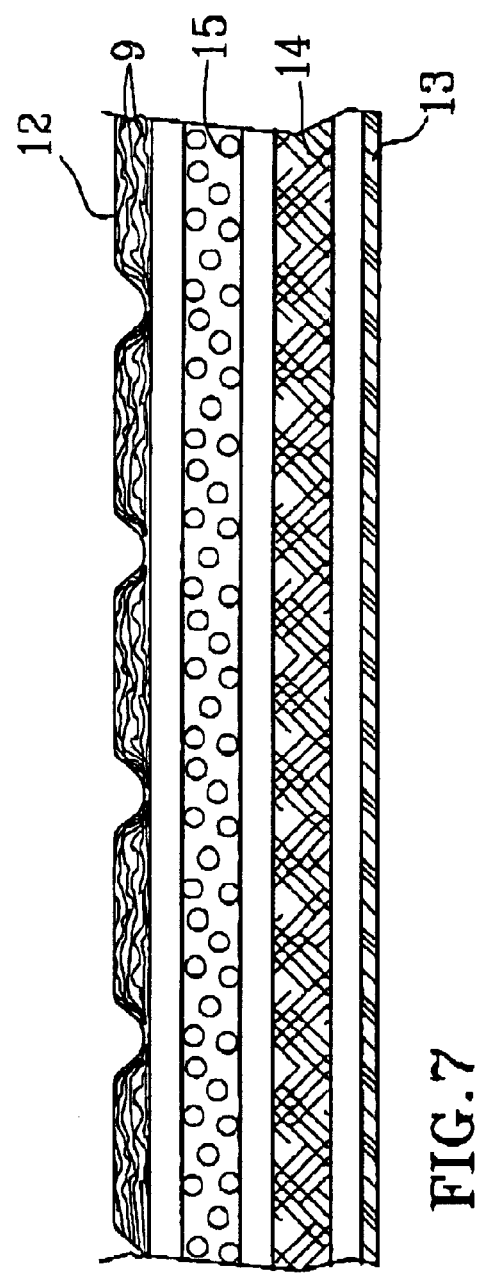

In FIG. 7, an alternative embodiment is shown, wherein the material layer 5 according to the invention has been used as a liquid pervious top layer. In this case, the basis weight should be at least 5 g/m$^2$, preferably within the interval 5–500 g/m$^2$, and most preferably 5–200 g/m$^2$, and the fibre thickness within the interval 0.5–50 dtex, preferably 1.5–25, and most preferably 2–15 dtex. In other respects, the material can be the same as described above. Underneath the material layer 5 applied as a top layer, an acquisition layer 15 of any optional type is arranged. The absorbent article according to FIG. 7 further comprises an absorbent body 4 and a liquid impervious back layer 3.

Figure 8:
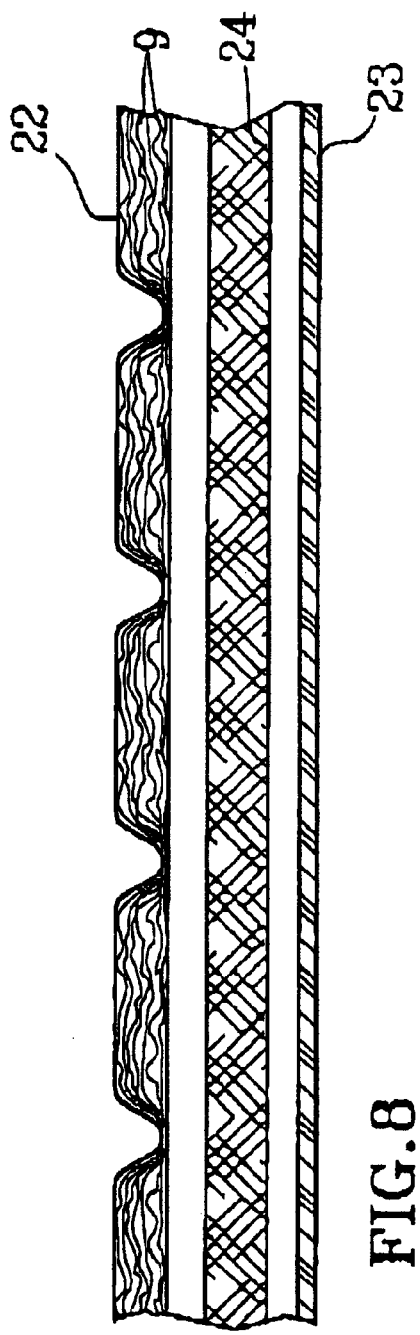

In the embodiment according to FIG. 8, the material layer 5 according to the invention has been used as a combined top layer and acquisition layer. In this case, the basis weight should be larger than 10 g/m$^2$, preferably be within the interval 10–1000 g/m$^2$, more preferably 30–700, and most preferably 30–350 g/m$^2$, and the fibre thickness within the interval 0.5–50 dtex, preferably 1.5–25, and most preferably 2–15 dtex. In a conventional way, the absorbent article according to FIG. 8 further comprises an absorbent body 4 and a liquid impervious back layer 3.

Figure 9:
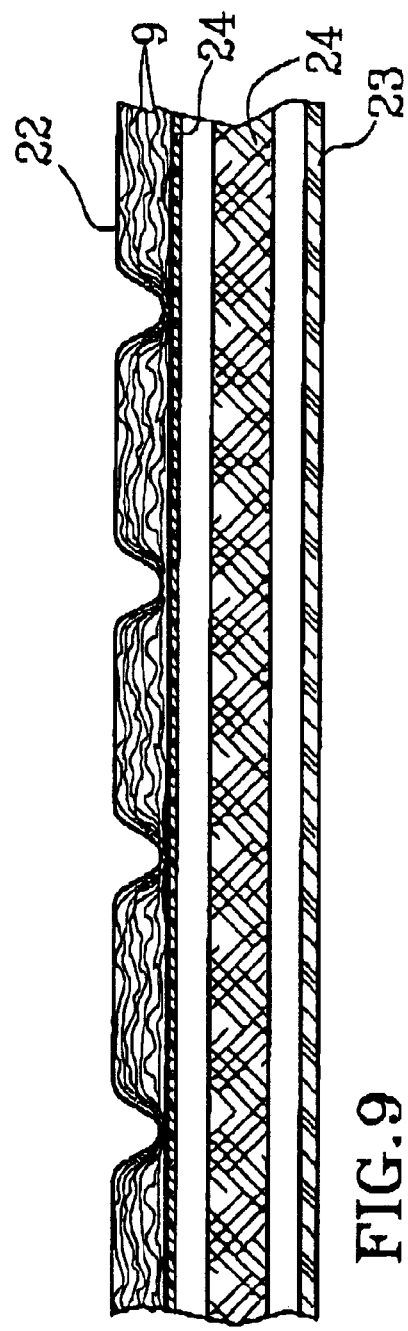

The embodiment according to FIG. 9 differs from what is shown in FIG. 8 in that a carrier material 22, e.g. in the form of a nonwoven, has been integrated on the underside of the combined top layer/acquisition layer 5. Such a carrier material can of course alternatively or furthermore be integrated with the upper side of the layer 5, or with the layer 5 according to FIG. 6 or FIG. 7.

In the embodiments according to FIGS. 7–9, the bonded fibre tow according to the invention will be directly contacting the skin of the wearer. In this case, extraordinary high demands are made on the comfort and softness of the material. Since the material consists of continuous fibres, there are no sharp, protruding fibre ends which may irritate the skin, but the material is very soft and pliable. In addition, it exhibits sufficient strength and wear resistance, due to the longitudinal continuous fibres 9, which provide strength in the longitudinal direction, and the bonding pattern, which provides strength in the transverse direction. In case part of the bonding pattern should break, the remaining parts of the pattern still exist.

As mentioned above, it is particularly advantageous if crimped or curled fibres are used in the tow, since they provide a particularly open and lofty structure. It is also possible to use a combination of straight and crimped fibres.

It is also possible to use different fibre types or different fibre thicknesses in different portions of the material, i.e. in different layers or regions thereof. This in order to create the desired absorption pattern. In this way, gradients of different hydrophilicity and pore size can be created. An admixture of superabsorbent fibres into the tow is also conceivable.

Figure 10:
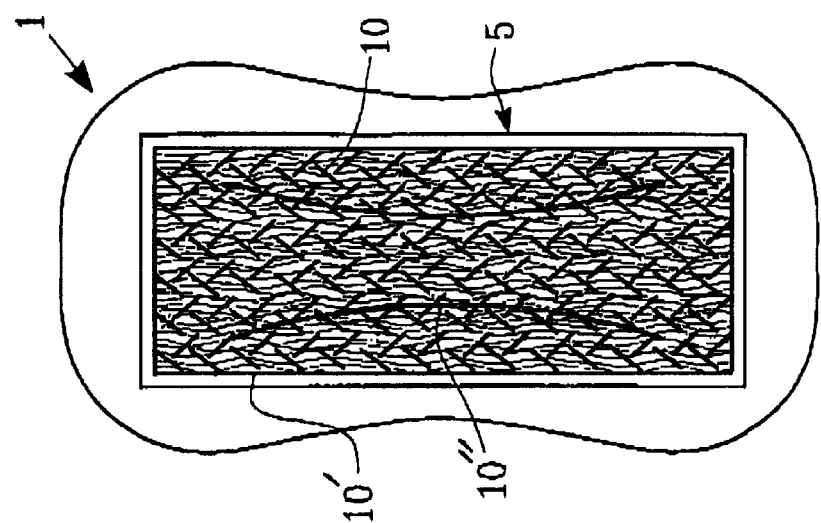
FIGS. 10–12 show schematic plan views of fibre layers according to the invention with varying bonding patterns across their surface.

FIG. 10 schematically shows a layer 5 according to the invention applied in an absorbent article 1, the outlines of which are indicated with dash-dot lines. In its central portion 5e, the layer 5 exhibits a relatively sparse bonding pattern 10, while it exhibits a significantly denser bonding pattern at its edge portions 5a and b. Thereby, it is assumed that the transverse edge portions 5a and b extend essentially transversely in relation to the longitudinal direction of the fibres in the layer 5, whereas the longitudinal edge portions 5c and d extend substantially along the longitudinal direction of the fibres. The layer 5 exhibits excellent liquid distributing properties in the longitudinal direction of the fibres, which is an advantage amongst other things in order to achieve a high utilization degree of the absorption capacity of the article 1. However, it may result in a certain risk for edge leakage from the transverse edge portions 5a and b. By means of making the bonding pattern more dense at the edge portions 5a and b, liquid is arrested or even prevented from spreading further. Furthermore, the dense bonding pattern along the edges provides an edge reinforcement of the layer. The sparse bonding pattern in the central portion 5e of the layer 5 creates an open structure which improves the liquid acquisition properties.

Figure 11:
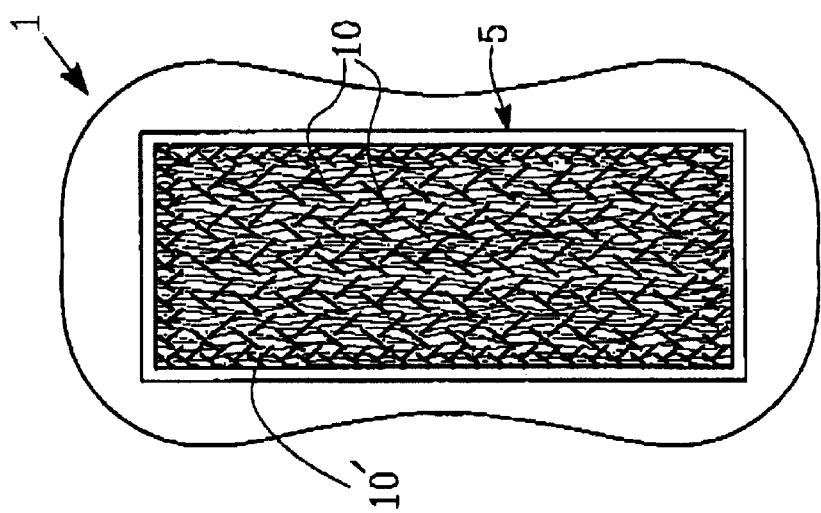

In FIG. 11, an encompassing, denser bonding pattern 10 is shown along both the transverse and the longitudinal edge portions 5a–d of the layer. Furthermore, the bonding pattern 10 comprises an encompassing continues barrier line or edge seal 10' which effectively prevents liquid from spreading outside the edges of the layer. Alternatively, such barrier lines 10' can be arranged only at some of the edge portions 5a–d, for example only at the transverse edge portions 5a and b.

Figure 12:
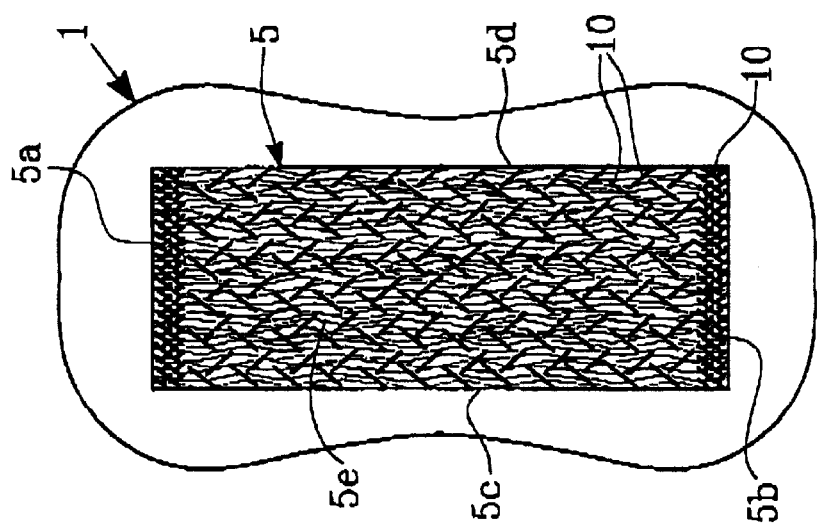

In the embodiment shown in FIG. 12, the bonding pattern 10 comprises a pair of arcuately curved distributing lines 10" intended to direct the liquid distribution in the layer 5 in a certain way. Furthermore, an encompassing barrier line 10' is provided along the edge portions 5a–d of the layer.

By means of braking the liquid spreading in the longitudinal and transverse direction of the layer 5 in different ways, the liquid is forced instead to pass further into the underlying absorption layers, something which is desirable since the layer 5 primarily is intended as a liquid acquisition layer which rapidly should receive and temporarily store liquid, before this is absorbed by the underlying absorbent body.

Figure 13:
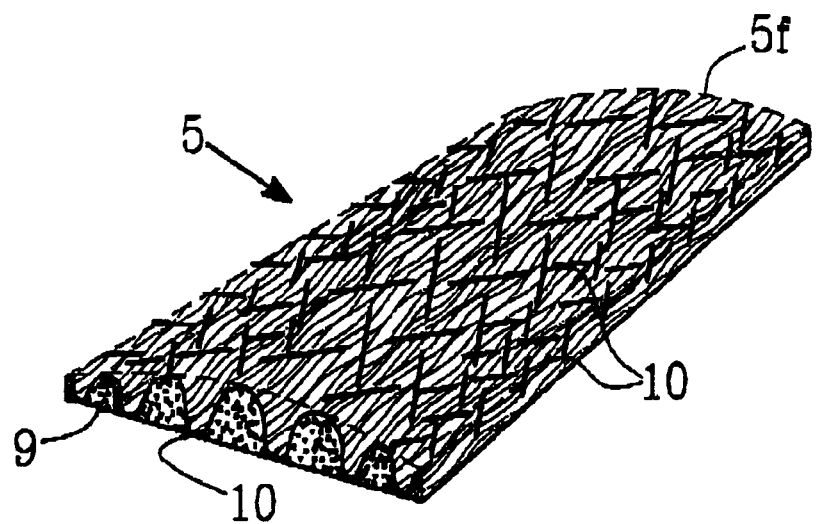
FIGS. 13 and 14 schematically show fibre layers having a three-dimensional shape, which has been obtained by means of a varying bonding pattern across the surface of the fibre layer.
Figure 14:
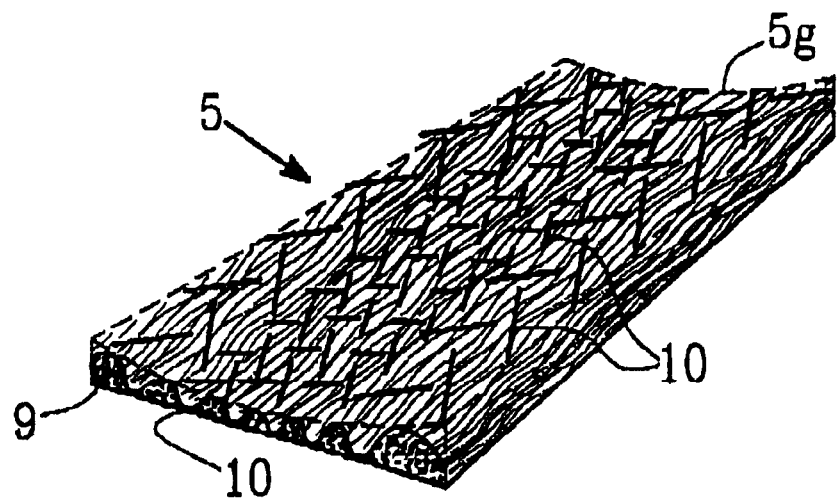

FIGS. 13 and 14 schematically show fibre layers 5 having a three-dimensional shape, wherein FIG. 13 shows a layer with a raised central portion 5e, and FIG. 14 shows a layer with a bowl-shaped central recess 5f. The raised central portion 5e achieves an improved contact with the body of the user and reduces the risk of leakage. The bowl-shaped recess 5f creates a liquid receiving volume, which also reduces the risk of leakage.

This three-dimensional shape is achieved by means of a varying bonding pattern 10 across the surface of the layer 5, possibly also combined with a varying basis weight in the different portions of the layer 5. By means of providing a more dense bonding pattern 10, a higher density is obtained and thereby a reduced thickness of the layer 5. If the basis weight is substantially uniform across the layer 5, a raised central portion according to FIG. 13 can be achieved just by means of providing a more sparse bonding pattern in the central portion than along the edges. In a corresponding way, a bowl-shape according to FIG. 14 can be achieved by means of providing a more dense bonding pattern in the central portion than along the edges. As mentioned above, a varying bonding pattern can be combined with a varying basis weight across the layer in order to create the desired three-dimensional shape.

The invention is of course not limited to what has been disclosed above and shown in the drawings, but a plurality of variations are conceivable within the scope of the claims.

What is claimed is:

1. An absorbent article, comprising:
    a liquid permeable top layer,
    a liquid impervious back layer,
    an absorbent body arranged therebetween, and
    a layer of continuous fibers which are bonded together in a bonding pattern, with the bonds creating open spaces beneath the top layer to allow for liquid distribution wherein the bonding pattern is different in different portions of said layer.

2. The absorbent article according to claim 1, wherein the bonding pattern is more sparse in a central, liquid acquisition, portion of the layer and is more dense in one or several edge portions of the layer.

3. The absorbent article according to claim 2, wherein the bonding pattern, along edge portions that are transverse to a longitudinal direction of the continuous fibers of the layer, exhibits a density that is sufficiently high to prevent liquid from spreading.

4. The absorbent article according to claim 3, wherein the bonding pattern in said transverse edge portions comprises at least one continuous barrier line which prevents liquid from spreading.

5. The absorbent article according to claim 1, wherein the bonding pattern, along encompassing edge portions of the layer, exhibits a density that is sufficiently high to prevent liquid from spreading.

6. The absorbent article according to claim 5, wherein the bonding pattern in said encompassing edge portions comprises at least one continuous barrier line which prevents liquid from spreading.

7. The absorbent article according to claim 1, wherein the layer exhibits one or several continuous directing lines for achieving a controlled liquid distribution in the layer.

8. The absorbent article according to claim 1, wherein the layer has a three-dimensional shape, including a raised central portion or a bowl-shaped central recess.

9. The absorbent article according to claim 1, wherein the bonding pattern is non-random.

10. The absorbent article according to claim 1, wherein the layer of continuous fibers is utilized as a liquid acquisition layer applied between the top layer and the absorbent body.

11. The absorbent article according to claim 10, wherein the layer of continuous fibers exhibits a basis weight of at least 10 g/m$^2$.

12. The absorbent article according to claim 10, wherein the top layer exhibits at least one hole, in an intended wetting area of the article, through which hole the liquid acquisition layer is exposed toward the user.

13. The absorbent article according to claim 10, wherein the layer of continuous fibers exhibits a basis weight of at least 5 g/m$^2$.

14. The absorbent article according to claim 10, wherein the layer of continuous fibers exhibits a basis weight between 10–1000 g/m$^2$.

15. The absorbent article according to claim 10, wherein the layer of continuous fibers exhibits a basis weight between 30–700 g/m$^2$.

16. The absorbent article according to claim 10, wherein the layer of continuous fibers exhibits a basis weight between 30–350 g/m$^2$.

17. The absorbent article according to claim 1, wherein the layer of continuous fibers is utilized as an integrated topsheet/liquid acquisition layer.

18. The absorbent article according to claim 15, wherein the layer of continuous fibers exhibits a basis weight between 10–1000 g/m$^2$.

19. The absorbent article according to claim 17, wherein the layer of continuous fibers exhibits a basis weight between 30–700 g/m$^2$.

20. The absorbent article according to claim 17, wherein the layer of continuous fibers exhibits a basis weight between 30–350 g/m$^2$.

21. The absorbent article according to claim 17, wherein the layer of continuous fibers exhibits a basis weight of at least 10 g/m².

22. The absorbent article according to claim 1, wherein at least a part of the continuous fibers in said layer are crimped or curled.

23. The absorbent article according to claim 1, wherein the bonding pattern comprises dots, spots or lines which cross a longitudinal direction of the continuous fibers.

24. The absorbent article according to claim 23, wherein different bonding lines over-lap each other, as seen in a transverse direction of the article, so that a main portion of the fibers are bonded at least at some part of their length.

25. The absorbent article according to claim 1, further comprising a carrier material for supporting the layer of continuous fibers.

26. The absorbent article according to claim 25, wherein the carrier material is a nonwoven material.

27. The absorbent article according to claim 1, wherein the fibers are tow.

28. An absorbent article, comprising:
a layer of continuous fibers which are bonded together in a bonding pattern, with the bonds creating channels along the surface of the layer to allow for liquid distribution, wherein the bonding pattern is different in different portions of the layer,
a liquid impervious back layer, and
an absorbent body therebetween.

29. The absorbent article according to claim 28, wherein the fibers are tow.

* * * * *